United States Patent [19]
Guenther et al.

[11] Patent Number: 4,900,381
[45] Date of Patent: Feb. 13, 1990

[54] METHOD FOR MANUFACTURING A MEASURING PROBE

[75] Inventors: Martin Guenther, Wildberg; Lothar Rupp, Aldingen, both of Fed. Rep. of Germany

[73] Assignee: Hewlett-Packard Company, Palo Alto, Calif.

[21] Appl. No.: 157,204

[22] Filed: Feb. 17, 1988

[30] Foreign Application Priority Data

Feb. 17, 1987 [EP] European Pat. Off. ........ 87102263.8

[51] Int. Cl.⁴ .......................... B32B 31/12; B32B 31/14
[52] U.S. Cl. ..................................... 156/90; 156/155; 156/289; 156/294; 156/305
[58] Field of Search ................. 156/155, 90, 294, 289, 156/305

[56] References Cited

U.S. PATENT DOCUMENTS

| | | | |
|---|---|---|---|
| 3,304,353 | 2/1967 | Harautuneian | 156/155 |
| 3,544,668 | 12/1970 | Dereniuk | 156/155 |
| 3,926,705 | 12/1975 | Todd | 156/289 |
| 4,557,900 | 12/1985 | Heitzmann | 422/55 |

FOREIGN PATENT DOCUMENTS 0073558  6/1982  European Pat. Off. .

OTHER PUBLICATIONS

Optical Fluorenscence and Its Application to an Intravascular Blood Gas Monitoring System, vol. BME-33, No. 2, Feb. 1986.
Fiber Optic pH Probe for Physiological Use; Anal. Chem. 1980, 52, 864–869.
A Miniature Fiber Optic pH Sensor for Physiological Use, Journal of Viomechanical Eng., May 1980; vol. 102.
Fiber-Optic Probe for in Vivo Measurement of Oxygen Partial Pressure, Anal. Chem, 1984, 56, 62–67.

Primary Examiner—George F. Lesmes
Assistant Examiner—J. Davis
Attorney, Agent, or Firm—Frank R. Perillo

[57] ABSTRACT

Probes, preferably optical probes for the invasive measurement of blood parameters consist of a plurality of sensors (or at least one sensor and a stabilizing core, or at least one single sensor), (11,17), each of these sensors (11,17) having a diffusion zone with a selective membrane (15) and all together surrounded by a stabilizing sheath (18); this sheath (18) is to be fastened on the sensor(s) (11,17) by a glue (22). A method is described for manufacturing such probes. This method includes the steps of covering the selective membrane (15) by a hardenable and soluble cover material (21), in particular a silicate, then fastening said sheath (18) on the sensors (11,17) by glue (22)—which cannot reach the selective membranes (15) as they are just covered by the cover material (21)—and then dissolving said cover material (21). This method guarantees that the selective membranes (15) are free of glue (22) after the manufacturing process.

8 Claims, 3 Drawing Sheets

METHOD FOR MANUFACTURING A MEASURING PROBE

This invention relates to a method for manufacturing a measuring probe, especially an optical probe for the invasive measurement of blood parameters such as pH, $pO_2$ or $PCO_2$, with at least one sensor having a selective membrane and a sheath at last partially covering said sensor and fastened on said sensor by a glue.

Probes for the invasive measurement of blood parameters consist of at least one sensor comprising an optical fiber, said fiber ending up with a gel zone containing a dye. The optical density or another optical parameter of that dye varies with the blood parameter (such as pH) to be measured. On the other side of the dye-containing gel, a reflector is positioned. The end of the fiber, the gel and the reflector are surrounded by a semi-permeable envelope (for example, a hydrogen ion permeable envelope in the case of a pH sensor) to keep the gel in place.

Light from this optical fiber passes through the dye-containing gel, is reflected by said reflector, passes the gel again and is transmitted through the optical fiber to an appropriate detector which measures light attenuation or changes in other optical parameters caused by the dye. This attenuation or change is a function of the blood parameter to be measured, and the relation between attenuation, absorbance or change of another optical parameter and the blood parameter is well-known.

Such a probe can be introduced into a patient's artery to measure—depending on the dye—various blood parameters such as pH, $pO_2$ or $pCO_2$.

A more detailed description of fiber optic pH measurement can be found in "A Miniature Fiber Optic pH Sensor for Physiological Use", Journal of Biomechanical Engineering, May 1980, p. 141.

A serious problem arises if more than one sensor or a sensor and a stabilizing core have to be combined in a single probe. This is the case, if more than one blood parameter shall be measured, or if the sensor needs stabilizing. In this case, the sensor(s) and/or the stabilizing core have to be coupled mechanically. This can be achieved by use of a sheath covering the front end of the probe and being appropriately perforated to allow the ions (in the case of a pH sensor) or the gas molecules (in the case of a $pO_2$ or a $pCO_2$ sensor) to reach the permeable envelope of the sensor, pass it and diffuse into the dye-containing gel. The sheath has to be secured by a glue or adhesive.

The most serious problem is that—when applying the glue to the sensor—the glue tends to move or creep along the same, thereby covering the diffusion zones of the selective membranes, i.e. the permeable envelopes in the region of the dye-containing gel. As a result, the ions or gas molecules cannot or hardly reach the selective membrane. Such a probe is either insensitive or has a very long time constant in the range of half an hour or more to render it unusuable.

It is a major objective of the present invention to propose a method for manufacturing a measuring probe which method prevents the glue from moving or creeping over a selective membrane when a sheath is fastened on the sensor(s).

According to the invention, this problem is solved by the following manufacturing steps:

(1) The selective membrane of the sensor is covered by a cover material which is
  (1.1) hardenable,
  (1.2) resistant to said glue,
  (1.3) soluble in a dissolvent which neither attacks said glue nor the probe components,
(2) the sheath is fastened on the sensor by said glue,
(3) the cover material is dissolved from the selective membrane by said dissolvent.

Typically, the sheath—which does not cover the diffusion zones, i.e. the selective membranes over the dye-containing gel—is loosely placed over the ends of some sensors each of them intended to measure a specific blood parameter. Then the cover material is applied onto the selective membranes (the region of the diffusion zones) and hardened. Preferably said cover material is air-hardenable. When the cover material has hardened, the glue is introduced between the sensors and the sheath through appropriate openings. These openings can be, for example, the front end of the sheath or special bores. The glue—for example, a two-component glue or an epoxy—then creeps along the sensor and the inside of the sheath and attaches the sensors to that sheath. The selective membranes are not covered by the glue as these selective membranes are just covered by the cover material which is resistant to the glue. When the glue has hardened, the cover material is dissolved in said dissolvent, preferably a fluid, which neither attacks the glue nor the probe components. In a preferred embodiment, this dissolvent is water, but other fluids such as alcohol also do not attack the glue or the probe components. A well-suited cover material for this purpose is silicate, for example a silicate consisting of $Na_2SiO_3$ and $Na_2SiO_5$ or a silicate consisting of $K_2SiO_3$ and $K_2SiO_5$. Other materials meeting the requirements are organic substances such as gelatine or pectine or a melt of polyethylenglycol (PEG). Such polyethylenglycol is melted at a temperature range of 40° to 50° C., applied to the selective membranes and hardened at room temperature. When the glue has also hardened, the PEG is soluble in water.

Of course, the described method is not restricted to a probe containing a plurality of optical sensors. For example, the probe can also consist of one or more than one sensor and a stabilizing core, for example, a wire or the like. This wire is used to stabilize the sensor(s) in the region of the diffusion zones. Typically, a diffusion zone consists of a dye-containing gel (covered by a membrane) and is mechanically not very stable.

The new method can also be used to manufacture other probes than optical ones. For example, it is also applicable if the sensor comprises an ion sensitive field effect transistor (ISFET) being covered by a selective membrane.

It is understood that the new method is also applicable if the sequence of process steps is in another order than explained above. For example, it is also possible to apply the glue to the sensor when the cover material has hardened and then to put the sheath over the sensors (in contrast to the process described above where the sheath is put over the sensors before applying the cover material and the glue).

A major advantage of the method according to the present invention is that a probe can be manufactured with a sheath covering the sensors partially, stabilizing them and fastened on them by a glue without the glue covering the selective membranes of the sensors and therefore not influencing the characteristics of the probe. Another advantage is that this method can be performed very easily, especially in a minimum of time and with a minimum of additional tools. A further advantage is that the glue does not have to be dosed exactly. Furthermore, the required materials are very cheap and easy to handle.

Of course, the new method is also applicable if the probe consists only of a single sensor (even without stabilizing core) and a sheath fastened on said sensor by a glue.

In the accompanying drawings, a preferred embodiment of the present invention is shown. More features and advantages of the invention arise from the following description in which these drawings are explained as well as the invention is described.

Figure 3:
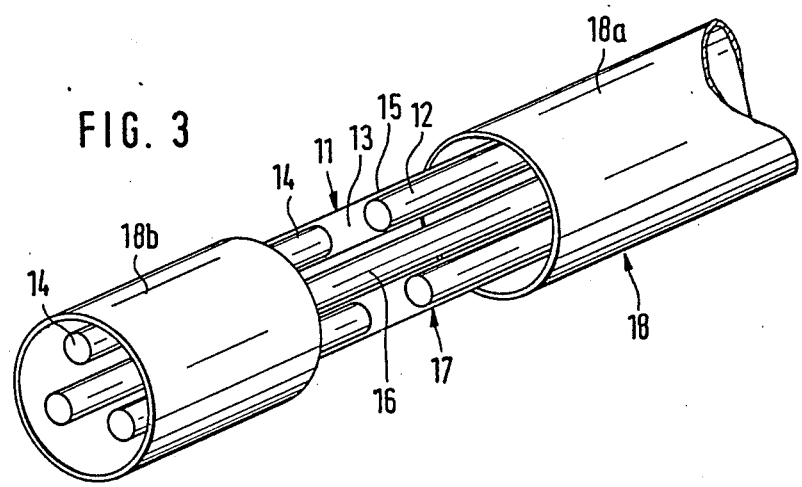
Figure 4:
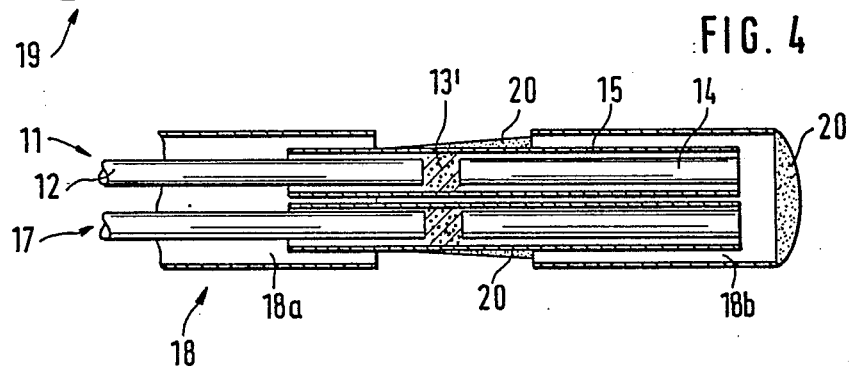
Figure 5A:
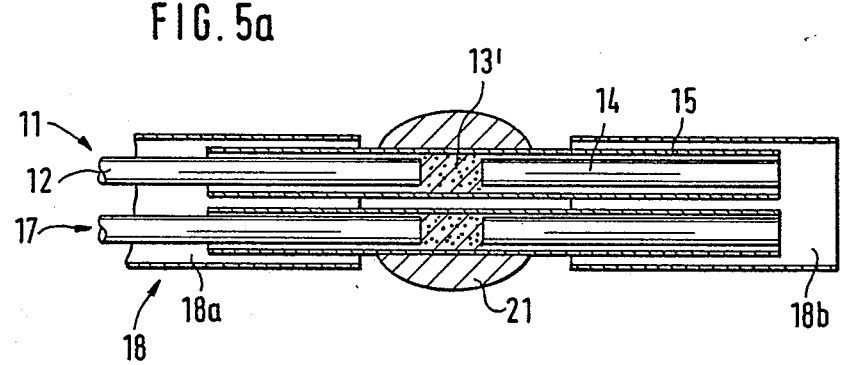
Figure 5B:
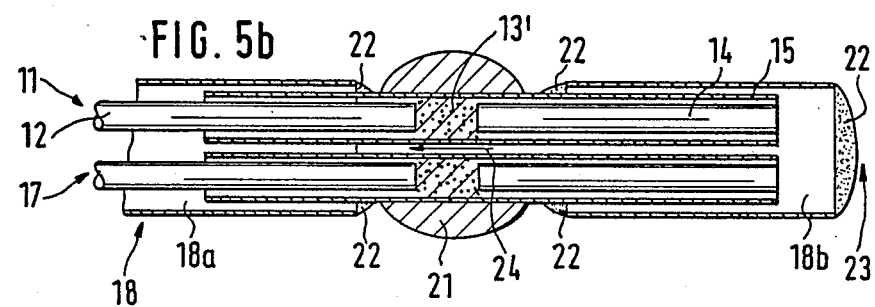
Figure 5C:
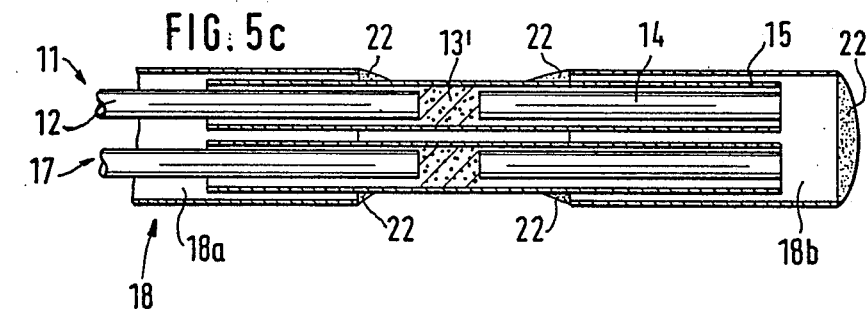
Figure 6:
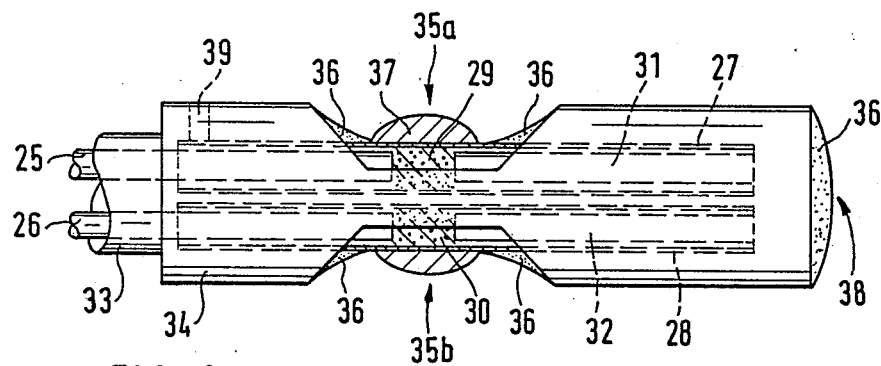
Figure 7:
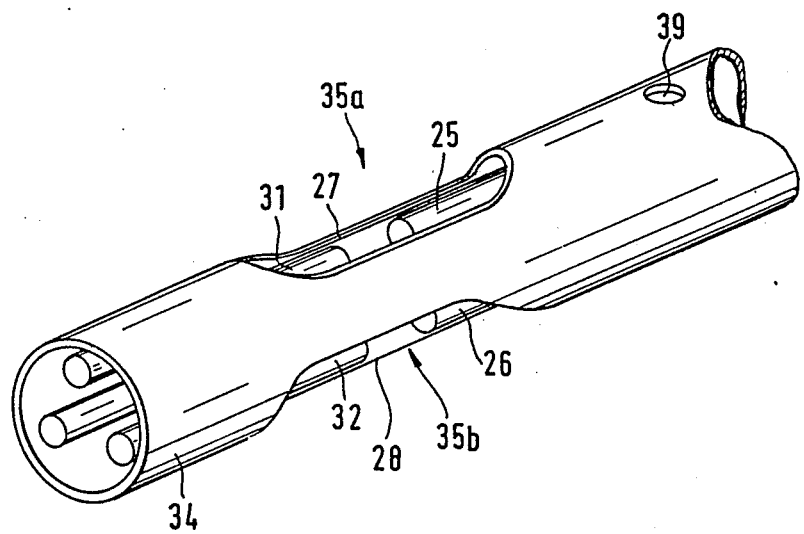

FIG. 3 is a perspective view of an optical probe containing a plurality of such sensors, FIG. 4 is a longitudinal section of this probe demonstrating unwanted creeping of a glue, FIGS. 5a to 5c show, using longitudinal sections of the end of a probe, the method according to the present invention, FIG. 6 shows a longitudinal section of another probe with another type of sheath and FIG. 7 is a perspective view of the probe of FIG. 6.

Figure 1:
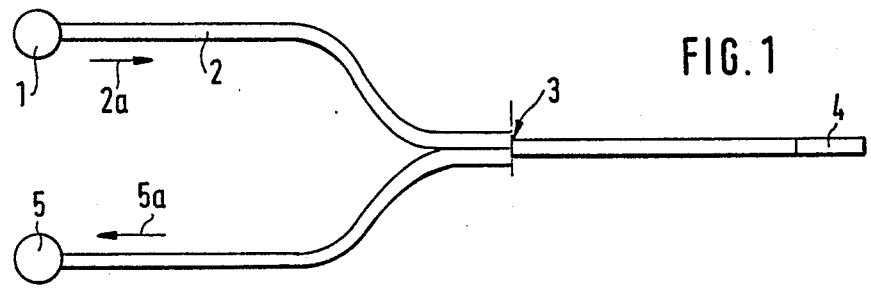
FIG. 1 shows an optical system for the measurement of blood parameters.

FIG. 1 shows a system for the invasive measurement of blood parameters, for example of the pH value. The light of an optical transmitter 1 is directed into an optical fiber 2 (see arrow 2a). Preferably, a plastic fiber is used which has the advantage that it cannot break off inside the body of a patient and that it can be sterilized by gamma rays. Usually a train of light pulses is used, but this is not a strict requirement. The light passes an optical coupler 3 and reaches tip 4 of the sensor said tip being intended to be introduced into the artery of a patient. Tip 4 of the sensor contains a gel into which a dye such as phenol red is immobilized. Said dye modifies at least one optical parameter, preferably the intensity, of the light depending on the pH (or, in other cases, $pO_2$ or $pCO_2$) value of the blood. The modified light is reflected into the same fiber and, passing through optical coupler 3, reaches an optical receiver 5 (see arrow 5a).

Figure 2:
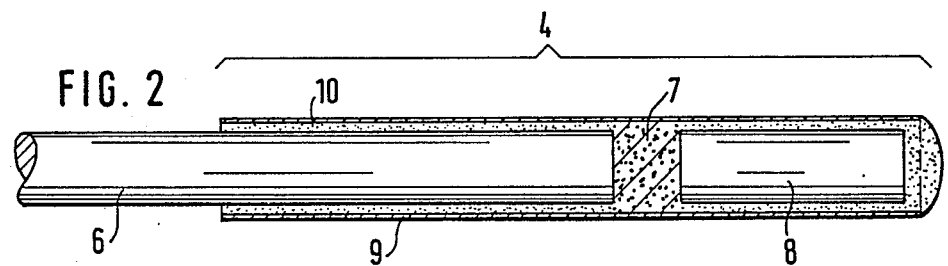
FIG. 2 is a longitudinal section of a single sensor.

FIG. 2 shows the details of tip 4 of an optical sensor using a system according to FIG. 1. Light directed in optical fiber 6 reaches a dye-containing gel 7, the absorption spectrum of said dye—for example, phenol red—being dependent on the pH value of the blood. The light is then reflected at reflector 8. Preferably, this reflector is made of metal such as platinum, the surface of this metal being polished on the side of gel 7. The whole system is packed in a selective membrane or envelope 9, this membrane being permeable for the ions or gas molecules to be measured—in case of a pH electrode for hydrogen ions—so that these ions/gas molecules can reach the dye-containing gel. Membrane 9 is fastened on the optical fiber 6 and the reflector 8 by a glue 10. The preferred material for membrane 9 is a hydrophilic material such as cellulose.

FIG. 3 is a perspective view of the end of an optical probe containing two optical sensors to measure various blood parameters such as, for example, pH, $pO_2$ or $pCO_2$. Each sensor consists of the fiber, a dye-containing gel, a reflector and permeable or selective membrane as described in the example of FIG. 2. For example, the pH sensor is generally referred to as numeral 11 and consists of the optical fiber 12, diffusion zone 13 (the dye-containing gel is not shown in this example) and reflector 14. The whole sensor is surrounded by a selective membrane 15. The $pO_2$ sensor is generally referred to as numeral 17. Instead of a $pO_2$ sensor, a $pCO_2$ sensor can also be used. The probe is also equipped with a stabilizing core, in this case a wire 16, which guarantees the mechanical stability of the probe especially in the region of the diffusion zones.

The two sensors—pH sensor 11 and $pO_2$ sensor 17—are surrounded by a sheath 18, for example, a polyimide sheath, fastened on sensors 11 and 17 and on wire 16 by a glue, for example a two-component glue. Said sheath must have at least one opening so that the patient's blood can be in contact with the diffusion zones. In the shown example, sheath 18 consists of two parts 18a and 18b which do not cover the diffusion zones of the single sensors.

The whole probe (reference numeral 19) is preferably intended to be introuduced into the artery of a patient for the purpose of measuring blood parameters. Therefore, this probe has to have a very small outer diameter. The probe of FIG. 3 has an outer diameter of 0.4 to 0.7 mm (the single sensors having a diameter of about 0.12 mm). Of course, it is also possible to introduce the probe into the vein of a patient.

The optical fibers are preferably polymethylmethacrylate (PMMA) light guides.

The mechanical design of FIG. 3 is, of course, not only applicable in the case that two blood parameter sensor have to be combined. It is also possible to combine more than two sensors; even a probe containing only one sensor can be surrounded by a sheath as shown in FIG. 3, in which case said sheath guarantees sufficient mechanical stability.

(In the following examples—see FIGS. 6 and 7—another sheath will be described which guarantees mechanical stability in the region of the diffusion zones, too.)

Another probe with the principal mechanical design of FIG. 3 consists of two optical fibers, one of them conducting light from the transmitter to the diffusion zone and another conducting the reflected light back to the receiver (differing from the arrangement shown in FIG. 1).

FIG. 4 is a longitudinal section of a probe as shown in FIG. 3. According to this section, the outer end of the probe is on the right-hand side and not on the left-hand side as in FIG. 3.

In the section of FIG. 4, for demonstration purposes only the two optical sensors 11 and 17 are shown, not the stabilizing wire. The components of the pH sensor—optical fiber 12, reflector 14 (a platinum wire with polished surface) and selective membrane 15—are the same as shown in FIG. 3. In the drawing of FIG. 4, the dye-containing gel in the diffusion zone is shown and referred to as 13'. The principal mechanical design of $pO_2$ sensor 17 is the same as that of pH sensor 11.

FIG. 4 shows the effect of fastening parts 18a and 18b of sheath 18 on the sensors by a glue. The glue 20 creeps along the sensors and thereby covers the diffusion zones, i.e. the selective membranes, which either makes the probe unusable or increases its time constant to unacceptable values. This effect is independent of the order of manufacturing steps, e.g. whether the sheath is first placed over the sensor and then the glue is applied through appropriate openings or whether the glue is first applied to the sensors and then the sheath is put over the same.

FIGS. 5a to 5c show—in a similar longitudinal section as FIG. 4—the method according to the invention which ensures that, after the manufacturing process, the selective membranes are free from glue so that the time constants are as short as possible. The reference numerals used are the same as in FIGS. 3 and 4 (although these figures do not show the new method).

According to FIG. 5a, the two parts 18a and 18b of sheath 18 are placed over the optical sensors. Then, a silicate solution 21 is spread on the diffusion zones and totally covers them. When the silicate has hardened (under the influence of air), the glue is introduced through openings of sheath 18 as shown in FIG. 15b. As the silicate has just hardened, the glue 22 cannot cover the diffusion zones of the sensors. The glue may, for example, be introduced through the front hole of part 18b (reference numeral 23) and/or through an opening of part 18a on the monitor side (not shown in FIG. 5b).

Depending on the silicate distribution, the glue may creep along the inner side of the sensors (shown by arrow 24). This is possible if the silicate covers only the outer surfaces of the sensors, e.g. the region of arrow 24 is free of silicate. In contrast, it is also possible to cover the sensor diffusion zones totally with silicate in which case the glue cannot creep along their inner surfaces.

When glue 22 has hardened, silicate 21 is dissolved in water. Water does not attack any of the probe components. FIG. 5c shows the end of the probe after removal of the silicate. Sheath 18 is now completely fixed to the optical sensors without covering the diffusion zones. The time constants of the blood parameter sensors are therefore not affected, i.e. the values to be measured can be displayed as fast as possible. The whole method does not need any aggressive dissolvents or increased temperature. It also ensures that there are no cavities inside the probe which could be dangerous in a medical application with respect to blood coagulation. Furthermore, the hardened glue 22 does not form any sharp edges which could be dangerous when introducing the probe into the body of a patient.

FIG. 6 shows a probe with another sheath before dissolution of the silicate.

Two sensors 25 and 26 are surrounded by selective membranes 27 and 28, each of them covering the dye-containing gels 29 and 30 as well as reflectors 31 and 32. On the transmitter/receiver side, these sensors are surrounded by a cable sheath 33. The front end sheath 34 is made of metal, in particular stainless steel, and has two openings 34a and 35b to allow the blood to reach the selective membranes of the sensors. Additionally, it guarantees good mechanical stability also in the region of the diffusion zones.

In the drawing of FIG. 6, the glue 36 has just hardened, but the silicate 37 is not yet dissolved in water. Like in the example of FIGS. 5a to 5c, the silicate protects the selective membranes so that they cannot be covered by the glue.

The manufacturing process for the probe shown in FIG. 6 is principally the same as for the probe shown in FIGS. 5a to 5c, i.e. glue 36 is introduced through front end opening 38 and an additional opening 39 of sheath 34 when the silicate has hardened.

FIG. 7 is a perspective view of the probe of FIG. 6 and offers an improved impression of sheath 34 and its openings 35a and 35b. Neither the glue nor the silicate are shown in this Figure.

We claim:

1. A method for manufacturing an optical probe for invasive measurement of blood parameters with at least one sensor having a selective membrane covering an indicator dye containing gel, and a sheath partially covering said sensor such that a portion of the selective membrane covering said gel is not covered by said sheath, said sheath being fastened on said sensor by a glue, said method comprising:
   (1) covering said portion of the selective membrane covering said gel with a cover material which is: hardenable, resistant to said glue; and soluble in a dissolvent which neither attacks said glue nor components on said probe;
   (2) fastening the sheath to the sensor by said glue; and
   (3) dissolving the cover material from the portion of the selective membrane by said dissolvent such that the portion of the selective membrane covering said gel is free from said glue.

2. Method according to claim 1, characterized in that said cover material is water-soluble.

3. Method according to claim 1 characterized in that said cover material is air-hardenable.

4. Method according to claim 1 characterized in that said cover material is a silicate.

5. Method according to claim 1 characterized in that said cover material is an organic substance.

6. Method according to claim 1, characterized in that said cover material is polyethylene glycol.

7. The method recited in claim 1 including an additional initial step of placing, but not attaching said sheath on said sensor.

8. Method according to claim 5 where said organic substance is chosen from the group consisting of gelatine and pectine.

* * * * *